(12) United States Patent
Taylor et al.

(10) Patent No.: US 6,657,019 B2
(45) Date of Patent: Dec. 2, 2003

(54) METHOD AND APPARATUS FOR PREDICTING POLYMER LATEX PROPERTIES IN AN EMULSION POLYMERIZATION PROCESS TO IMPROVE THE QUALITY AND PRODUCTIVITY OF THE POLYMER LATEX

(75) Inventors: Michael A. Taylor, Rock Hill, SC (US); Jonathan P. Antonucci, Rock Hill, SC (US); Robert R. Racz, Charlotte, SC (US)

(73) Assignee: BASF Corporation, Southfield, MI (US)

(*) Notice: Subject to any disclaimer, the term of this patent is extended or adjusted under 35 U.S.C. 154(b) by 0 days.

(21) Appl. No.: 09/988,459

(22) Filed: Nov. 20, 2001

(65) Prior Publication Data

US 2003/0100632 A1 May 29, 2003

(51) Int. Cl.$^7$ .................................................. C08F 2/00
(52) U.S. Cl. ....................... 526/59; 422/109; 422/110; 422/111; 714/51; 526/335
(58) Field of Search ................................ 422/109, 110, 422/111; 714/51; 526/59, 335

(56) References Cited

U.S. PATENT DOCUMENTS

| | | | |
|---|---|---|---|
| 3,276,844 A | * | 10/1966 | Davison et al. |
| 5,650,722 A | | 7/1997 | Smith et al. ................. 324/307 |
| 6,073,055 A | | 6/2000 | Jahn et al. .................... 700/97 |
| 6,093,211 A | | 7/2000 | Hamielec et al. ............. 703/12 |
| 6,144,897 A | | 11/2000 | Selliers ........................ 700/269 |

FOREIGN PATENT DOCUMENTS

| | | | | |
|---|---|---|---|---|
| WO | WO 00/22489 | 4/2000 | .......... | G05B/17/02 |
| WO | WO 01/25863 | 4/2001 | .......... | G05B/17/02 |

* cited by examiner

Primary Examiner—David W. Wu
Assistant Examiner—William K. Cheung

(57) ABSTRACT

The present invention is a method for predicting polymer latex properties for an emulsion polymer latex based on statistical relationships between the polymer latex properties and process parameters for the emulsion polymerization process. The method for predicting one or more polymer latex properties for an emulsion polymer latex according to the invention includes conducting an emulsion polymerization process in a reactor including one or more reactor inputs to produce an emulsion polymer latex, measuring a set of process parameters for the emulsion polymerization process, performing a heat balance and a mass balance across the reactor based on the set of measured process parameters to determine a set of calculated polymer latex properties for the emulsion polymerization process, and determining one or more predicted polymer latex properties for the emulsion polymer being prepared in the emulsion polymerization process using the measured process parameters, the calculated polymer latex properties, and a set of predetermined statistical relationships between the process parameters and the polymer latex properties to be predicted. The present invention also includes an apparatus and a computer program product for predicting the polymer latex properties of an emulsion polymer latex.

18 Claims, 9 Drawing Sheets

METHOD AND APPARATUS FOR PREDICTING POLYMER LATEX PROPERTIES IN AN EMULSION POLYMERIZATION PROCESS TO IMPROVE THE QUALITY AND PRODUCTIVITY OF THE POLYMER LATEX

FIELD OF THE INVENTION

The present invention relates to a method and apparatus for predicting the properties of a polymer latex in an emulsion polymerization process and more particularly relates to a method and apparatus of using the predicted polymer latex properties to monitor and adjust the process parameters of an emulsion polymerization process to improve the quality and productivity of the process and the emulsion polymer latices produced therefrom.

BACKGROUND OF THE INVENTION

One common method for producing polymers such as homopolymers and copolymers is emulsion polymerization. In a typical emulsion polymerization process, monomers are combined with an initiator in the presence of a surfactant in an aqueous medium and the monomers are polymerized to form the polymer. For example, the monomers can be combined with a surfactant and water to form a pre-emulsion and the pre-emulsion and initiator separately fed to a reactor where the polymerization reaction occurs to form the polymer. Alternatively, the monomers, an aqueous surfactant solution and an initiator can each be fed separately to the reactor.

It is important that the polymer latices produced in the emulsion polymerization process are consistent and of good quality. To ensure acceptable product quality, it has traditionally been necessary to take samples of the polymer latex at various stages or times during the emulsion polymerization process. Analytical tests are then conducted on the samples to verify that the samples are of sufficient quality. If the analytical tests do not produce values within certain specified limits, the process is modified to alter the product such that the product is of sufficient quality.

One drawback to the traditional method of process quality control is that it takes time to receive the results from the analytical tests. Accordingly, the emulsion polymerization process must be delayed resulting in reduced production. In addition, the sampling and testing is retrospective and does not allow the process to be proactively controlled. Furthermore, taking and analyzing samples can be expensive. Therefore, there is a need to provide a method of proactively controlling an emulsion polymerization process that produces a quality product without reducing the amount of the latex polymer produced and without increasing the cost of the process.

SUMMARY OF THE INVENTION

The present invention provides a method for predicting polymer latex properties for an emulsion polymer latex based on statistical relationships between the polymer latex properties and process parameters. The method of the invention allows for real-time control of the emulsion polymerization process and thus facilitates the production of a quality emulsion polymer without the need to stop production for sampling and analytical testing. The method of the invention also provides feedback and feed forward control of the emulsion polymerization process to ensure the production of a quality product without increasing the cost of production. Furthermore, the statistical relationships between the polymer latex properties and process parameters determined for a specific emulsion polymerization process can advantageously be used to predict the polymer latex properties for another emulsion polymerization process making generally the same polymer. The method of the invention can be used with continuous, batch and semi-batch emulsion polymerization processes.

The method for predicting one or more polymer latex properties for an emulsion polymer latex according to the invention includes conducting an emulsion polymerization process in a reactor including one or more reactor inputs to produce an emulsion polymer latex, measuring a set of process parameters for the emulsion polymerization process, performing a heat balance and a mass balance across the reactor based on the set of measured process parameters to determine a set of calculated polymer latex properties for the emulsion polymerization process, and determining one or more predicted polymer latex properties for the emulsion polymer latex being prepared in the emulsion polymerization process using process parameters selected from one or more of said set and said second set and a predetermined set of statistical relationships between the selected process parameters and the polymer latex properties to be predicted. The heat balance and mass balance are typically conducted using a set of measured process parameters including the mass of ingredients initially added to the reactor, the flow rates for the reactor inputs, the temperatures for the reactor inputs, the flow rates and temperatures for the input and output of a coolant stream communicating with the reactor, and the temperature and pressure of the reactor, to determine a set of calculated process parameters such as the monomer/polymer ratio in the reactor. The one or more predicted polymer latex properties for the emulsion polymer are preferably determined using the reactor temperature, the flow rates for the reactor inputs, the monomer/polymer ratio and a predetermined set of statistical relationships between the reactor temperature, the flow rates for the reactor inputs, the monomer/polymer ratio and the polymer latex properties to be predicted.

In accordance with the invention, the set of statistical relationships between the process parameters and the polymer latex properties used are preferably determined by first operating the emulsion polymerization process using a plurality of varying process parameters and measuring the polymer latex properties and then calculating the set of statistical relationships between the process parameters and polymer latex properties for the emulsion polymerization process based on the process parameters and the measured polymer latex properties. In addition to the measured polymer latex properties, polymer latex properties such as the monomer/polymer ratio calculated by performing a heat balance and mass balance across the system can be used to determine the statistical relationships. Preferably, the process parameters used to provide the set of statistical relationships are selected from the group consisting of the reactor temperature and the flow rates for the reactor inputs. In addition, the measured and calculated polymer latex properties are preferably selected from the group consisting of the monomer/polymer ratio, the number of polymer particles, the amount of polymer crosslinking, the molecular weight of the polymer, the concentration of Diels-Alder adducts and the polymer particle size. Preferably, the monomer/polymer ratio, the flow rates for the reactor inputs, the reactor temperature, and the statistical relationships are used to predict polymer latex properties such as the number of polymer particles, the amount of polymer crosslinking, the molecular weight of the polymer, the concentration of Diels-Alder adducts and the polymer particle size.

The predicted polymer latex properties can be used in various ways to provide a more consistent emulsion polymer product. For example, the predicted polymer latex properties can be compared to predetermined upper and lower limits for the polymer latex properties. If the predicted polymer latex properties are not within the predetermined upper and lower limits for the polymer latex properties, a sample of the emulsion polymer from the emulsion polymerization reaction can be taken and the actual polymer latex properties from the sample measured to determine if the process parameters for the emulsion polymerization reaction should be adjusted. Alternatively, the process parameters for the reactor or for further processing steps downstream from the reactor can be adjusted if the predicted polymer latex properties are not within the predetermined upper and lower limits for the polymer latex properties to provide feedback or feed forward control. The predicted polymer latex properties can also be analyzed using statistical process control methods to determine whether the predicted polymer latex properties are acceptable and whether process parameters for the emulsion polymerization process or for further processing steps downstream from the reactor need to be adjusted. The processing steps downstream from the reactor can include at least one of a redox treatment step, a steam stripping step and an agglomeration step and the process parameters that can be adjusted include the amount of redox chemicals in the redox treatment step, the addition time for the redox treatment step, the amount of steam in the stripping step, the stripping time in the steam stripping step, the temperature of the steam stripping step, and the pressure in the agglomeration step.

The present invention also includes an apparatus for predicting the polymer latex properties of an emulsion polymer latex using the process parameters for the emulsion polymerization reaction. The apparatus includes a reactor including one or more reactor inputs for producing an emulsion polymer latex, means for measuring a set of process parameters for the emulsion polymerization process communicating with the reactor, means for performing a heat balance and a mass balance across the reactor based on the set of process parameters to determine a set of calculated polymer latex properties for the emulsion polymerization process, the performing means communicating with the measuring means, and means for determining one or more predicted polymer latex properties for the emulsion polymer being prepared in the emulsion polymerization process using process parameters selected from one or more of the set and the second set and a predetermined set of statistical relationships between the selected process parameters and the polymer latex properties, the determining means communicating with the measuring means and the performing means. Preferably, the reactor further includes a coolant stream and said measuring means measures a set of process parameters that includes the mass of ingredients initially added to the reactor, the flow rates for the reactor inputs, the temperatures for the reactor inputs, the flow rate and temperatures for the coolant stream input and output, and the temperature and pressure of the reactor. In addition, the means for performing a heat balance and a mass balance across the reactor based on the set of process parameters is preferably used to determine the monomer/polymer ratio in the reactor. The determining means preferably determines one or more predicted polymer latex properties for the emulsion polymer using the reactor temperature, the flow rates for the reactor inputs, the monomer/polymer ratio and a predetermined set of statistical relationships between the reactor temperature, the flow rates for the reactor inputs, the monomer/polymer ratio and the polymer latex properties to be predicted.

In addition to the above, the apparatus also preferably includes means for measuring polymer latex properties for the emulsion polymerization process and means for calculating the set of statistical relationships between the process parameters and polymer latex properties for the emulsion polymerization process based on the measured process parameters and measured and calculated polymer latex properties, the calculating means communicating with the means for measuring a set of process parameters, the means for measuring polymer latex properties, the performing means and the determining means, wherein the determining means uses the statistical relationships calculated by the calculating means to determine the one or more predicted polymer latex properties. The means for measuring a set of process parameters can measure process parameters selected from the group consisting of the reactor temperature and the flow rates for the reactor inputs. The means for measuring polymer latex properties can measure polymer latex properties selected from the group consisting of the monomer/polymer ratio, the number of polymer particles, the amount of polymer crosslinking, the molecular weight of the polymer, the concentration of Diels-Alder adducts and the polymer particle size. The performing means typically calculates the monomer/polymer ratio for the reactor. The determining means preferably uses the monomer/polymer ratio, the flow rates for the reactor inputs, the reactor temperature, and the statistical relationships from the calculating means to determine predicted polymer latex properties selected from the group consisting of the number of polymer particles, the amount of polymer crosslinking, the molecular weight of the polymer, the concentration of Diels-Alder adducts and the polymer particle size.

In a preferred embodiment of the invention, the apparatus further includes means for comparing the predicted polymer latex properties to predetermined upper and lower limits for the polymer latex properties. The apparatus can then further include means for adjusting the process parameters for the reactor if the predicted polymer latex properties are not within predetermined upper and lower limits for the polymer latex properties. Alternatively, the apparatus can include one or more additional processing stages such as those described above for the emulsion polymerization process downstream from said reactor and means for adjusting the process parameters for the additional processing stages if the predicted polymer latex properties are not within predetermined upper and lower limits for the polymer latex properties. The apparatus can further include statistical process control means for analyzing the predicted polymer latex properties to determine whether the predicted polymer latex properties are acceptable and means for adjusting the process parameters for the emulsion polymerization process if the predicted polymer latex properties are not acceptable. Alternatively, if the apparatus includes an additional processing stage as discussed above, the statistical process control means can analyze the predicted polymer latex properties to determine whether the predicted polymer latex properties are acceptable and the apparatus can include means for adjusting the process parameters for the additional processing stages.

In an alternative embodiment of the invention, the apparatus for predicting the properties of a polymer latex formed by an emulsion polymerization process includes first processing means for performing a heat balance and a mass balance for a reactor including one or more reactor inputs in an emulsion polymerization process to determine a set of calculated polymer latex properties for the emulsion polymerization process based on a set of measured process parameters and second processing means communicating with the first processing means for determining one or more predicted properties for the polymer latex using the calculated polymer latex properties determined by the first processing means, the set of measured process parameters, and a set of predetermined statistical relationships between the process parameters and the polymer latex properties to be predicted. In addition, the apparatus can include processing means communicating with the first processing means for analyzing the actual properties for a polymer latex and the process parameters for the emulsion polymerization process to determine statistical relationships between the polymer latex properties and the process parameters for use in determining the predicted polymer latex properties. The apparatus can also include processing means communicating with the second processing means for comparing the predicted polymer latex properties to predetermined upper and lower limits. The apparatus can also include a control system for adjusting process parameters for the reactor or for processing steps downstream of the reactor if the predicted polymer latex properties are not within the predetermined upper and lower limits for the polymer latex properties. The apparatus can also include processing means for analyzing the calculated polymer latex properties determined by the first processing means, the set of measured process parameters, and the predicted polymer latex properties determined by the second processing means to determine if the predicted polymer latex properties are acceptable and if the process parameters for the reactor or for processing steps downstream from the reactor need to be adjusted.

The present invention also further includes a computer program product for predicting the properties of an emulsion polymer latex that includes a computer-readable storage medium having computer readable program code means embodied in the medium. The computer-readable program code means includes first computer instruction means for performing a heat balance and a mass balance across a reactor for an emulsion polymerization process to determine a set of calculated polymer latex properties for the emulsion polymerization process using a set of measured process parameters and second computer instruction means for determining one or more predicted polymer latex properties for the emulsion polymer latex being prepared in the emulsion polymerization process using the set of calculated polymer latex properties, the set of measured process parameters, and a set of predetermined statistical relationships between the calculated process parameters, the measured process parameters and the polymer latex properties to be predicted. The computer program product preferably also includes instruction means for determining the set of statistical relationships between the process parameters and polymer latex properties used by the second computer instruction means based on a plurality of varying process parameters for the emulsion polymerization process and polymer latex properties measured from the emulsion polymerization process. The computer program can also include computer instruction means for comparing the predicted polymer latex properties to predetermined upper and lower limits for the polymer latex properties. Furthermore, the computer program product can include computer instruction means for analyzing the set of calculated process parameters, the set of measured process parameters and the predicted polymer latex properties using statistical process control methods to determine if the predicted polymer latex properties are acceptable and if the process parameters for the emulsion polymerization process or for processing steps downstream of the emulsion polymerization process need to be adjusted.

These and other features and advantages of the present invention will become more readily apparent to those skilled in the art upon consideration of the following detailed description and accompanying drawings, which describe both the preferred and alternative embodiments of the present invention.

DETAILED DESCRIPTION OF THE PREFERRED EMBODIMENTS

In the following detailed description and accompanying drawings, preferred embodiments are described in detail to enable practice of the invention. Although the invention is described with reference to these specific preferred embodiments, it will be understood that the invention is not limited to these preferred embodiments. But to the contrary, the invention includes numerous alternatives, modifications and equivalents as will become apparent from consideration of the following detailed description and accompanying drawings. Like numbers refer to like elements throughout.

Figure 1:
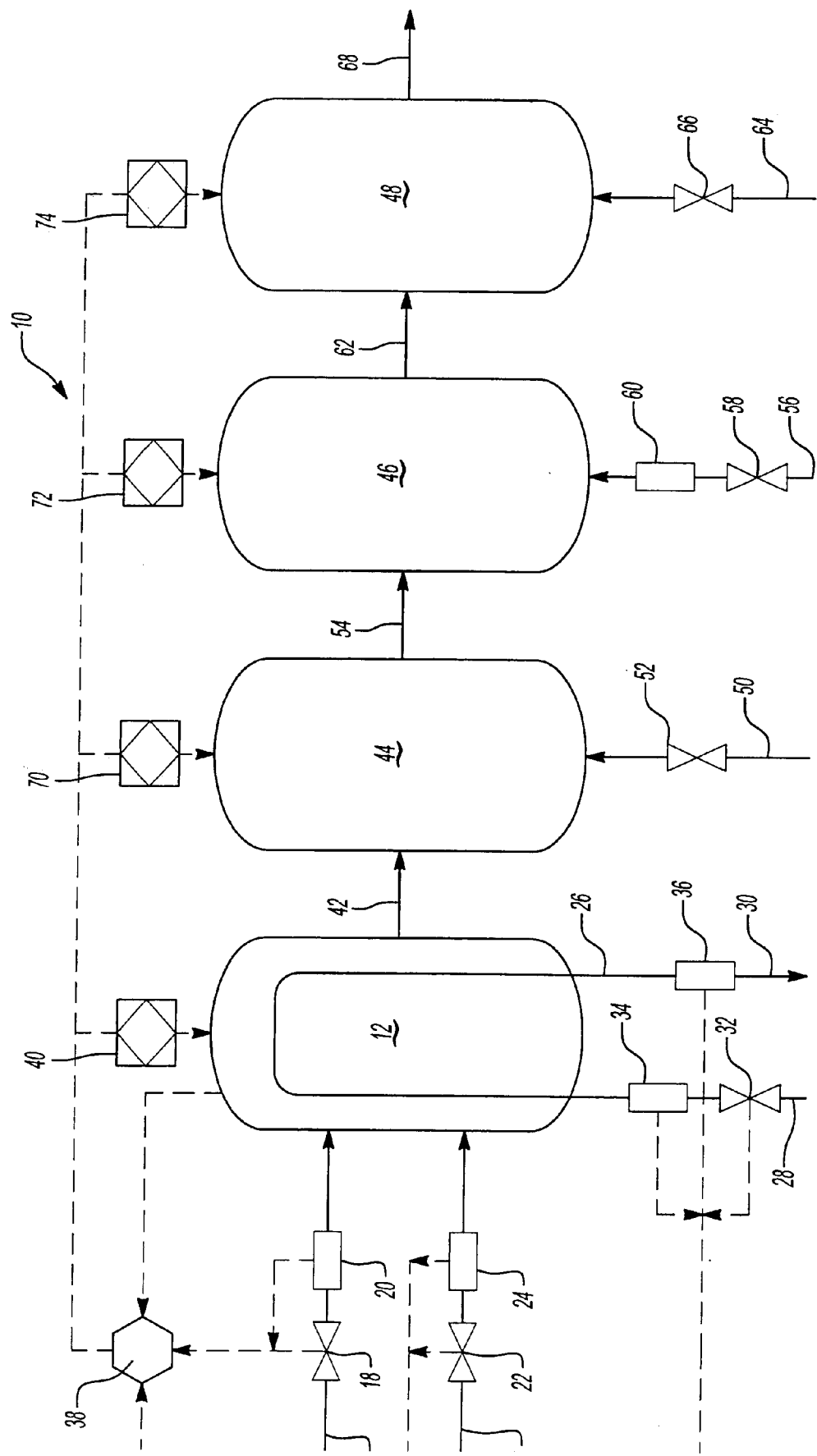
FIG. 1 is a schematic drawing of an emulsion polymerization process including a reactor and processing steps downstream from the reactor, and an apparatus for predicting polymer latex properties in accordance with the invention.

FIG. 1 illustrates an exemplary emulsion polymerization process 10 for use in the invention. Although FIG. 1 illustrates a continuous emulsion polymerization process 10, the present invention can also be used with batch and semi-batch emulsion polymerization processes. The emulsion polymerization process 10 includes a reactor 12 and one or more reactor inputs such as reactor input 14 and reactor input 16. Although FIG. 1 illustrates a single reactor 12 and two reactor inputs, the emulsion polymerization process 10 can also be conducted using a series of reactors and varying numbers of reactor inputs as would be readily understood by those skilled in the art.

The reactor inputs 14 and 16 can include a monomer or pre-emulsion stream and an initiator stream. The monomer stream can include one or more monomers that can be used to produce the emulsion polymer. The term "polymer" as used herein refers to homopolymers (made from one monomer) and copolymers (made from two or more monomers). In addition to monomers, the monomer stream can include a surfactant, a seed latex, water, and other desired components. The initiator stream can include at least one initiator or initiator system that is used to cause the polymerization of the monomers in the monomer stream. The initiator stream can also include a surfactant, water, and other desired components. In addition to these input streams, contents can be initially fed to the reactor 12 prior to feeding the monomer and initiator streams as would be understood by those skilled in the art. As shown in FIG. 1, the reactor input 14 can include a flow rate meter 18 for measuring the flow rate of the reactor input stream and a thermometer 20 for measuring the temperature of the reactor input stream. The reactor input 16 also includes a flow rate meter 22 for measuring the flow rate of the reactor input stream and a thermometer 24 for measuring the temperature of the reactor input stream. The flow rate meters 18 and 22 (and the other flow rate meters discussed herein) preferably measure the mass flow rate of the input streams 14 and 16 but can measure other flow rates (e.g. volumetric flow rates) as long as enough information is provided to perform a heat and mass balance of the reactor as discussed in more detail below.

In addition to the input streams 14 and 16, the reactor 12 typically includes a coolant stream 26 that is in heat transfer communication with the reactor 12 for cooling the reactor contents. The coolant stream includes a coolant stream input 28 and a coolant stream output 30. The coolant stream input includes a flow rate meter 32 for measuring the flow rate of the coolant input stream and a thermometer 34 for measuring the temperature of the coolant input stream. The coolant output stream also includes a thermometer 36 for measuring the temperature of the coolant output stream.

As illustrated by the dashed lines in FIG. 1, the flow rate meter 18, the thermometer 20, the flow rate meter 22, the thermometer 24, the flow rate meter 32, the thermometer 34 and the thermometer 36 communicate with a processor 38 and provide flow rate and temperature readings to the processor. In addition, a thermometer and pressure gauge (not shown) communicating with the reactor 12 also communicate with the processor 38 and provide temperature and pressure readings to the processor. The processor 38 communicates with a process control unit 40 that in turn communicates with the reactor 12, the reactor inputs 14 and 16 and the coolant stream 26 to control process parameters for the reactor such as the flow rates of the reactor inputs and coolant stream; the temperatures of the reactor, reactor inputs, and coolant stream input and outputs; and the pressure of the reactor. As would be readily understood by those skilled in the art, the flow rates of the reactor inputs 14 and 16 also control the reaction time in the reactor 12.

The reactor 12 in the continuous process also includes a reactor output 42 that can communicate with additional processing units such as a redox treatment unit 44, a steam stripping unit 46 and a physical agglomeration unit 48. The redox treatment unit 44 includes an input stream 50 that includes a flow rate meter 52 for measuring the flow rate of the input stream. The input stream provides reducing and oxidizing agents to the emulsion polymer latex formed by the reactor 12, to reduce the monomer content of the latex. The resulting latex can then be fed through an outlet 54 to the steam stripping unit 46, which uses a steam feed 56 to help remove any unreacted monomer from the latex. The steam feed includes a flow rate meter 58 for measuring the flow rate of the steam feed and a thermometer 60 for measuring the temperature of the steam feed. The latex can then be fed through an outlet 62 to a physical agglomeration unit 48 that includes an optional chemical agglomeration input 64 and an optional flow rate meter 66 that measures the flow rate of the chemical agglomeration input. The chemical agglomeration input 64 can provide agglomeration chemicals for treatment of the latex if a chemical agglomeration is to be performed. The resulting agglomerated latex is fed through output 68 and can be collected for storage or transport. Although FIG. 1 illustrates a redox treatment unit 44, a steam stripping unit 46 and an agglomeration unit 48, other processing units downstream from the reactor 12 can also be included in the emulsion polymerization process 10. In addition, the process 10 can operate without any of the redox treatment unit 44, the steam stripping unit 46 and the agglomeration unit 48.

As shown by the dashed lines, the processor 38 can communicate with a process control unit 70 that in turn communicates with the redox treatment unit 44 to control process parameters for the redox treatment unit such as the flow rate of the redox chemicals and the treatment time for the latex. The processor 38 can also communicate with a process control unit 72 that in turn communicates with the steam stripping unit 46 to control process parameters for the steam stripping unit such as the flow rate of the steam feed 56, the temperature of the steam feed, and the stripping time for the latex. Moreover, the processor 38 can also communicate with a process control unit 74 that in turn communicates with the agglomeration unit 48 to control process parameters for the agglomeration unit such as the pressure of the agglomeration unit.

FIGS. 2–6 are flow diagrams illustrating various embodiments of the invention for determining predicted polymer latex properties and using them to control the emulsion polymerization process. As shown in step 78, the present invention preferably first includes the step of conducting the emulsion polymerization process 10 using varying process parameters and measuring the polymer latex properties of the resulting emulsion polymer latex. For example, process parameters such as the mass of ingredients initially added to the reactor 12, the flow rates and temperatures for the reactor inputs 14 and 16, the flow rates and temperatures for the coolant stream input 28 and output 30, and the temperature and pressure of the reactor, can be varied in accordance with the invention to determine the effects on the resulting polymer latex properties. In addition, other process parameters can also be varied in accordance with the invention such as the amount of seed latex used if a seed latex is indeed used to produce the polymer. The polymer latex properties that can be measured based on the changes to the process parameters include but are not limited to the monomer/polymer ratio, the number of polymer particles, the amount of polymer crosslinking, the molecular weight of the polymer, the concentration of Diels-Alder adducts and the polymer particle size, and suitable methods for measuring these polymer latex properties are known to those skilled in the art. Certain polymer latex properties such as the monomer/polymer ratio can also be calculated, e.g., through the use of a heat balance and mass balance, as discussed below. The process parameters and polymer latex properties can be measured during the normal operation of the emulsion polymerization process 10 or the process parameters intentionally varied to provide a broader range of data points for the process parameters and polymer latex properties.

The process next typically includes the step 80 of performing a heat balance and a mass balance across the reactor 12 to determine a set of calculated polymer latex properties. Typically, the heat balance and mass balance are conducted using process parameters such as the mass of ingredients initially added to the reactor 12, the flow rates and temperatures for the reactor inputs 14 and 16, the flow rates and temperatures for the coolant stream input 28 and output 30, and the temperature and pressure of the reactor. These values can be sent to a processing means such as processor 38 to perform the heat balance and mass balance and thus to provide the set of calculated polymer latex properties. For example, the heat balance and mass balance can be used to determine the monomer/polymer ratio in the reactor 12. The monomer/polymer ratio can also be described as the amount of monomer conversion or the monomer conversion profile as it relates to the process as a whole over time.

The process of the invention next includes the step 82 of determining statistical relationships between the process parameters and polymer latex properties. In particular, statistical analysis is used to determine the relationships between certain measured process parameters and calculated or measured polymer latex properties such as those discussed above. For example, in a preferred embodiment of the invention, statistical relationships can be determined between the reactor temperature, the flow rates for the reactor inputs 14 and 16, the monomer/polymer ratio, the number of polymer particles the amount of polymer crosslinking, the molecular weight of the polymer, the number of Diels-Alder adducts, and the polymer particle size. The measured process parameters and calculated or measured polymer latex properties can be sent to processing means such as processor 38 to determine the statistical relationships between the process parameters and polymer latex properties. The statistical relationships can be based on a set of constants that are specific to a particular polymer and process type (i.e., continuous, batch or semi-batch). For example, a particular polymer latex property to be predicted (P) may be statistically related to process parameters or to other polymer latex properties (Q, R, S) by a suitable algorithm such as the following formula (wherein A, B, C, X, Y and Z are constants): $P=AQ^X+BR^Y+CS^Z$. The statistical relationships can be used along with the process parameters and calculated polymer latex properties to predict polymer latex properties for the emulsion polymerization process 10. In addition, the statistical relationships can advantageously be used for other emulsion polymerization processes that make the same or a substantially similar polymer using the same type of process (i.e., continuous, batch or semi-batch).

Once the statistical relationships between the process parameters and polymer latex properties have been determined as shown in step 82, the actual emulsion polymerization process 10 can be conducted as shown in step 84 and a set of process parameters for the emulsion polymerization process measured as shown in step 86. The term "set" as used herein can include one or more of a particular element. The process parameters measured are typically the same as the process parameters measured in step 78 and are usually measured using the same equipment used to measure the process parameters in step 78. Any additional process parameters needed to perform the heat balance and mass balance as discussed below can also be measured.

The process next includes the step 88 of performing a heat balance and a mass balance across the reactor 12 to determine a set of calculated polymer latex properties. Typically, the heat balance and mass balance are conducted using process parameters such as the mass of ingredients initially added to the reactor 12, the flow rates and temperatures for the reactor inputs 14 and 16, the flow rates and temperatures for the coolant stream input 28 and output 30, and the temperature and pressure of the reactor. These values can be sent to a processing means such as processor 3 8 to perform the heat balance and mass balance and thus to provide the set of calculated polymer latex properties. For example, the heat balance and mass balance can be used to determine the monomer/polymer ratio in the reactor 12.

As shown in step 90, the predicted polymer latex properties are then determined based on the measured process parameters from step 86, the calculated polymer latex properties from step 88, and the statistical relationships from step 82 between the measured process parameters, the calculated polymer latex properties and the polymer latex properties to be predicted. For example, these values can be sent to processing means such as processor 38 to determine the predicted polymer latex properties. Various polymer latex properties can be predicted such as the number of polymer particles, the amount of polymer crosslinking, the molecular weight of the polymer, the concentration of Diels-Alder adducts and the polymer particle size, can be predicted. The resulting predicted polymer properties eliminate the cost and time associated with taking periodic samples from the reactor 12 to verify that the polymer latex produced in the emulsion polymerization process 10 is desirable.

Figure 2:
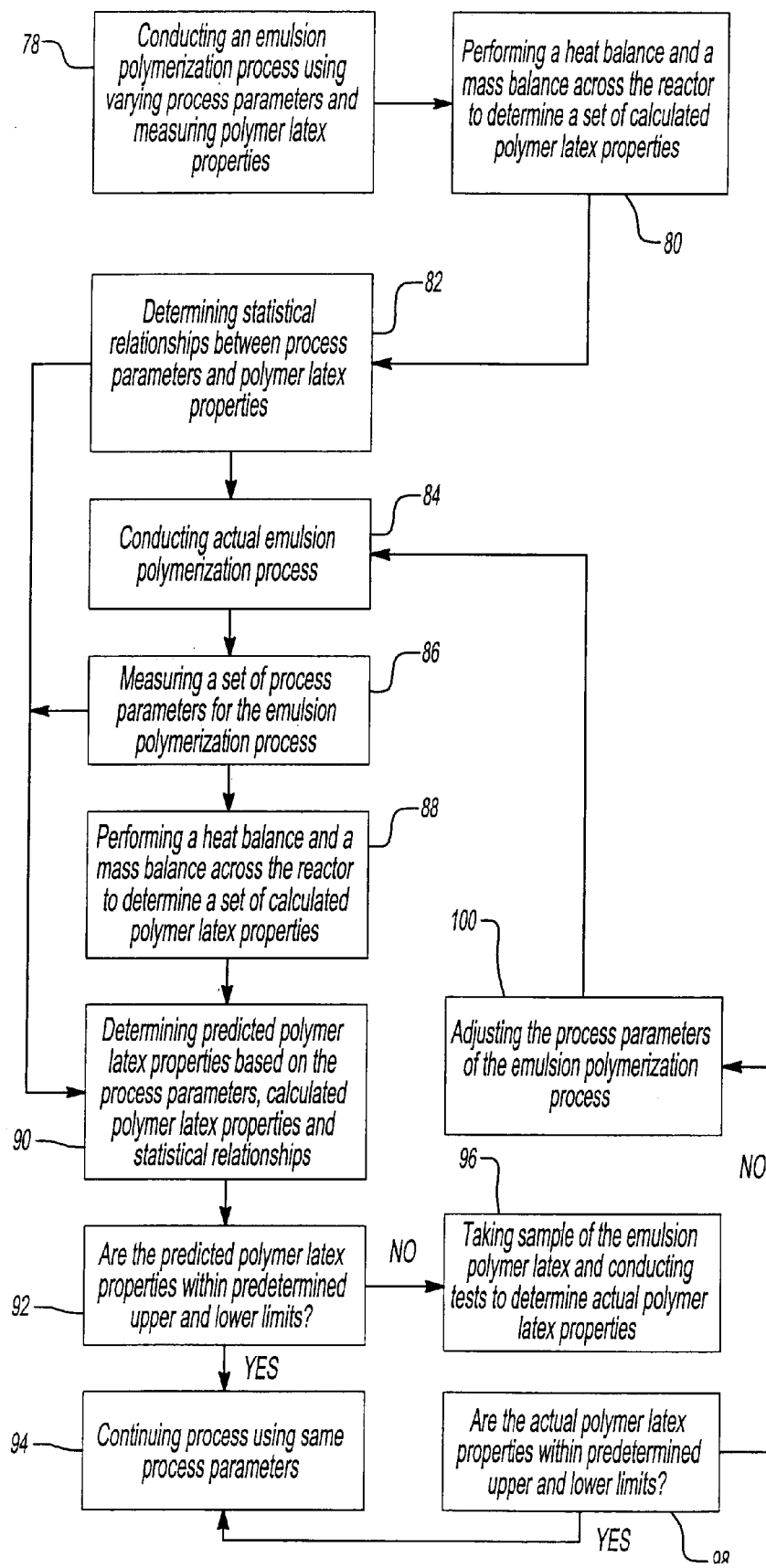
FIG. 2 is a flow diagram according to the invention illustrating the emulsion polymerization process, the method of predicting polymer latex properties, and the use of the predicted polymer latex properties to determine whether samples of the polymer latex need to be taken and tested.

Once the predicted polymer latex properties are determined, they can be used various ways in the emulsion polymerization process 10. For example, FIG. 2 illustrates one embodiment of the invention wherein the predicted polymer latex properties are used to prompt the operator of the emulsion polymerization process 10 to take samples and conduct tests. In particular, processing means such as processor 38 can be used to verify that the predicted polymer properties are within predetermined upper and lower limits for the polymer properties (see step 92). For example, predetermined upper and lower limits for various polymer latex properties can be provided for each type of polymer produced by the process and these values can be stored by a storage means (not shown) communicating with processing means such as the processor 38. The predicted polymer properties can then be compared to one or more polymer properties having stored upper and lower limits to determine if the predicted polymer properties are within the upper and lower limits. If the predicted polymer properties are within the predetermined upper and lower limits, the emulsion polymerization process 10 can be continued using the same process parameters as shown in step 94. On the other hand, if the predicted polymer properties are not within the predetermined upper and lower limits, an operator can take a sample of the emulsion polymer latex and conduct tests to determine the actual polymer latex properties as shown in step 96. If the actual polymer latex properties are within the predetermined upper and lower limits then the emulsion polymerization process 10 can be continued using the same process parameters as shown in step 94. However, if the actual polymer latex properties are not within the predetermined upper and lower limits, the process parameters for the emulsion polymerization process 10 can then be adjusted as shown in step 100. For example, the operator or processing means can determine what changes need to be made to the process parameters and the process parameters of the reactor 12, the reactor inputs 14 and 16 and the coolant stream 26 can be adjusted accordingly. The operator or processing means can alternatively determine what changes need to be made to the process parameters for additional downstream processing units and these process parameters can be adjusted; however, because of the time needed to obtain the test results, it is preferred to use the results of the sample to provide feedback control of the emulsion polymerization process 10 and not feed forward control of the additional downstream processing units.

Figure 3:
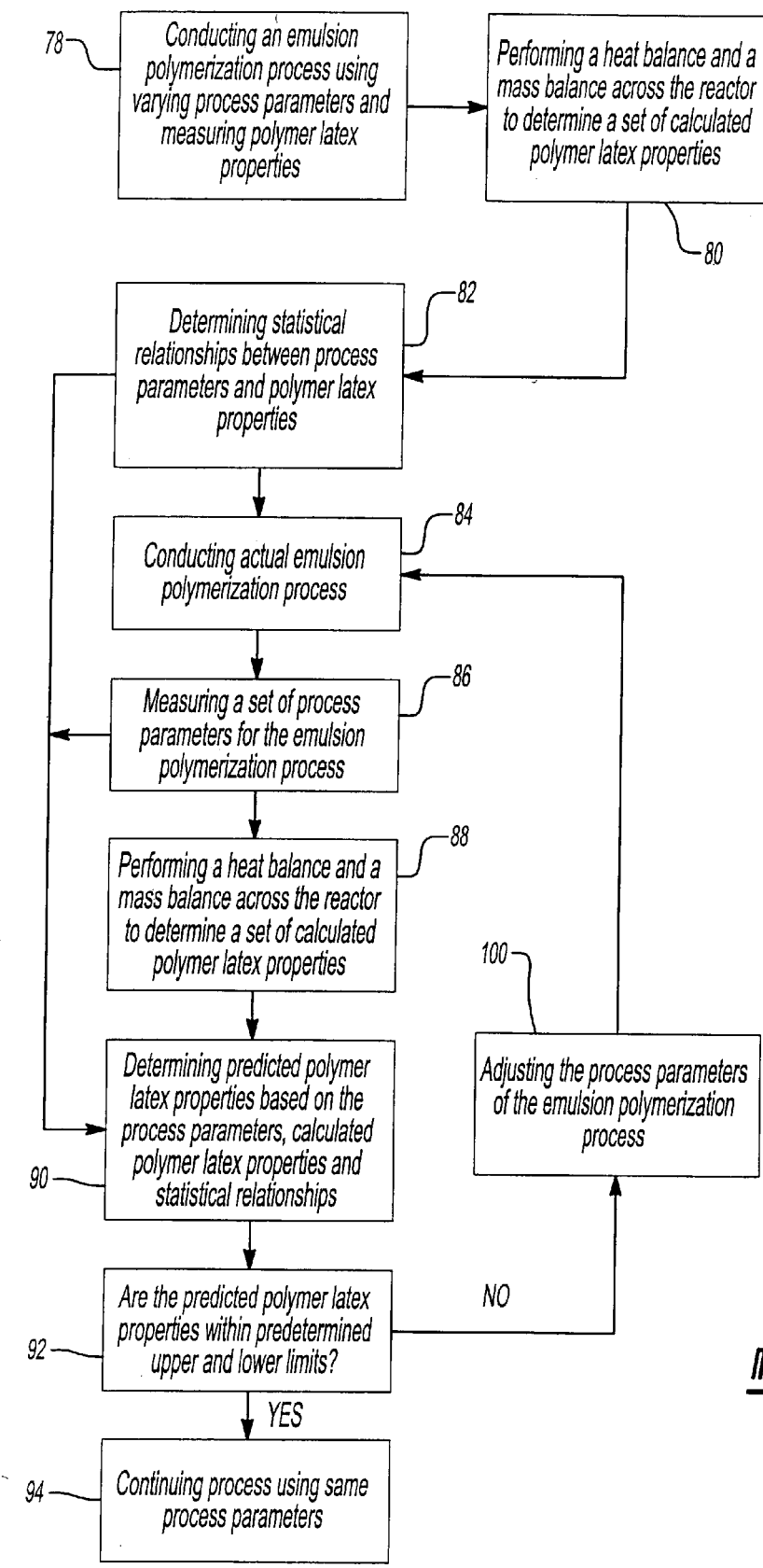
FIG. 3 is a flow diagram according to the invention illustrating the emulsion polymerization process, the method of predicting polymer latex properties, and the use of feedback control to adjust the process parameters of the emulsion polymerization process if the predicted polymer latex properties are not within predetermined upper and lower limits.

FIG. 3 is a flow diagram illustrating an alternative embodiment of the invention where predicted polymer latex properties are used directly for feedback control. In particular, processing means such as processor 38 can be used to verify that the predicted polymer properties are within predetermined upper and lower limits for the polymer properties as shown in step 92. If the predicted polymer properties are within the predetermined upper and lower limits, the emulsion polymerization process 10 can be continued using the same process parameters as shown in step 94. On the other hand, if the predicted polymer properties are not within the predetermined upper and lower limits, the process parameters for the emulsion polymerization process 10 can be adjusted as shown in step 100. For example, the processor 38 can determine what changes need to be made to the process parameters and communicate the changes to the process control unit 40, which in turn can communicate the changes to the reactor 12, the reactor inputs 14 and 16 and the coolant stream 26.

Figure 4:
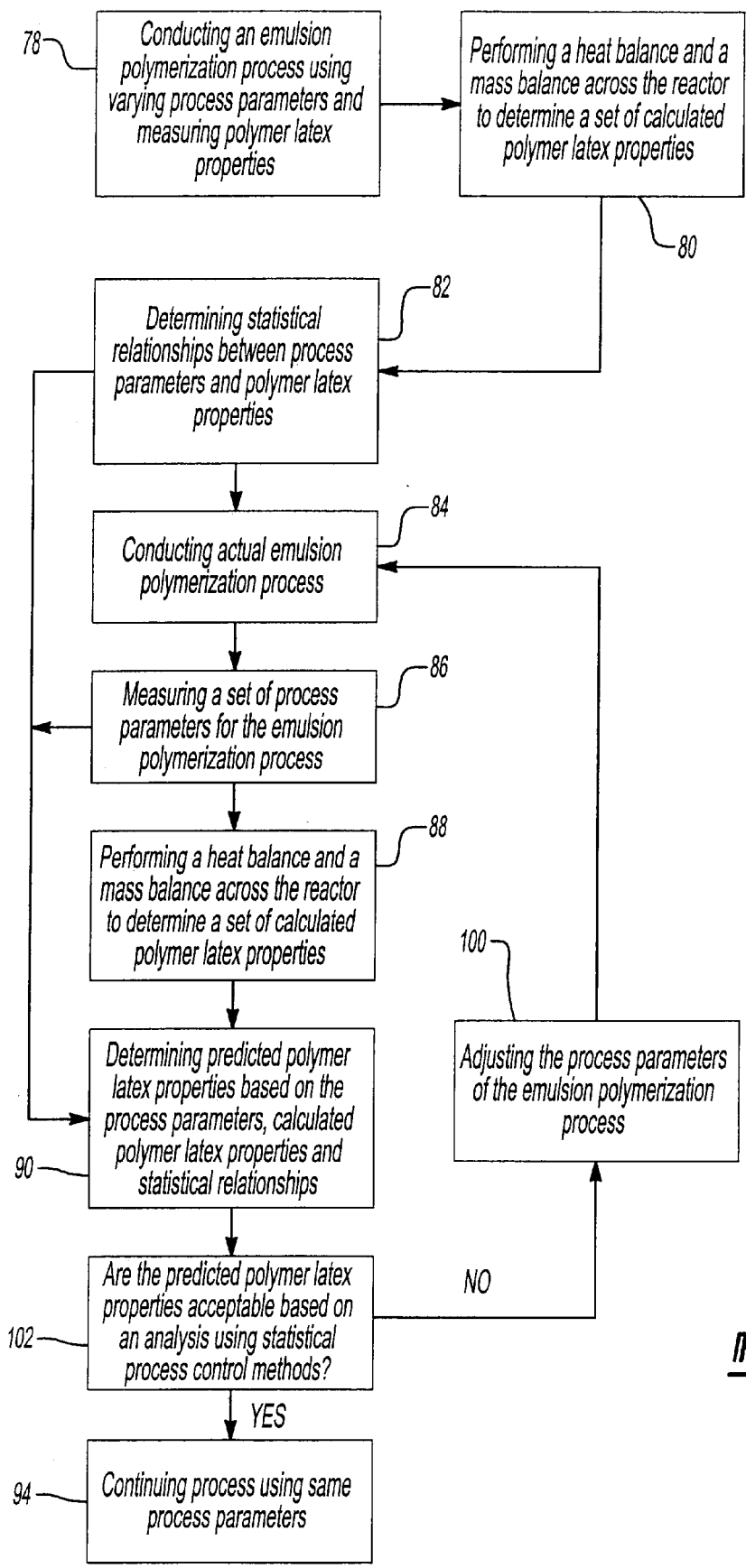
FIG. 4 is a flow diagram according to the invention illustrating the emulsion polymerization process, the method of predicting polymer latex properties, and the use of feedback control to adjust the process parameters of the emulsion polymerization process if the predicted polymer latex properties are not acceptable based on a statistical process control analysis of the predicted polymer latex properties.

FIG. 4 is a flow diagram illustrating another embodiment of the invention where a statistical analysis of the predicted polymer latex properties is used to determine whether the polymer latex is of acceptable quality and if feedback control of the process parameters is desired. In particular, processing means such as processor 38 can be used to analyze the predicted polymer latex properties from step 90 using statistical process control methods known in the art to determine if the predicted polymer latex properties are acceptable as shown in step 102. The statistical analysis typically uses various algorithms to identify undesirable trends in the predicted polymer latex properties over time. For example, if a number consecutive batches of a product showed either a progressive increase or a progressive decrease in one of the predicted properties, such a trend in the predicted polymer properties could be considered unacceptable. If the predicted polymer latex properties are acceptable, the polymer latex is presumed to be of acceptable quality and the emulsion polymerization process 10 can be continued using the same process parameters as shown in step 94. However, if the predicted polymer properties are not acceptable, the process parameters for the emulsion polymerization process 10 can be adjusted as shown in step 100. For example, the processor 38 can determine what changes need to be made to the process parameters and communicate the changes to the process control unit 40, which in turn can communicate the changes to the reactor 12, the reactor inputs 14 and 16 and the coolant stream 26.

Figure 5:
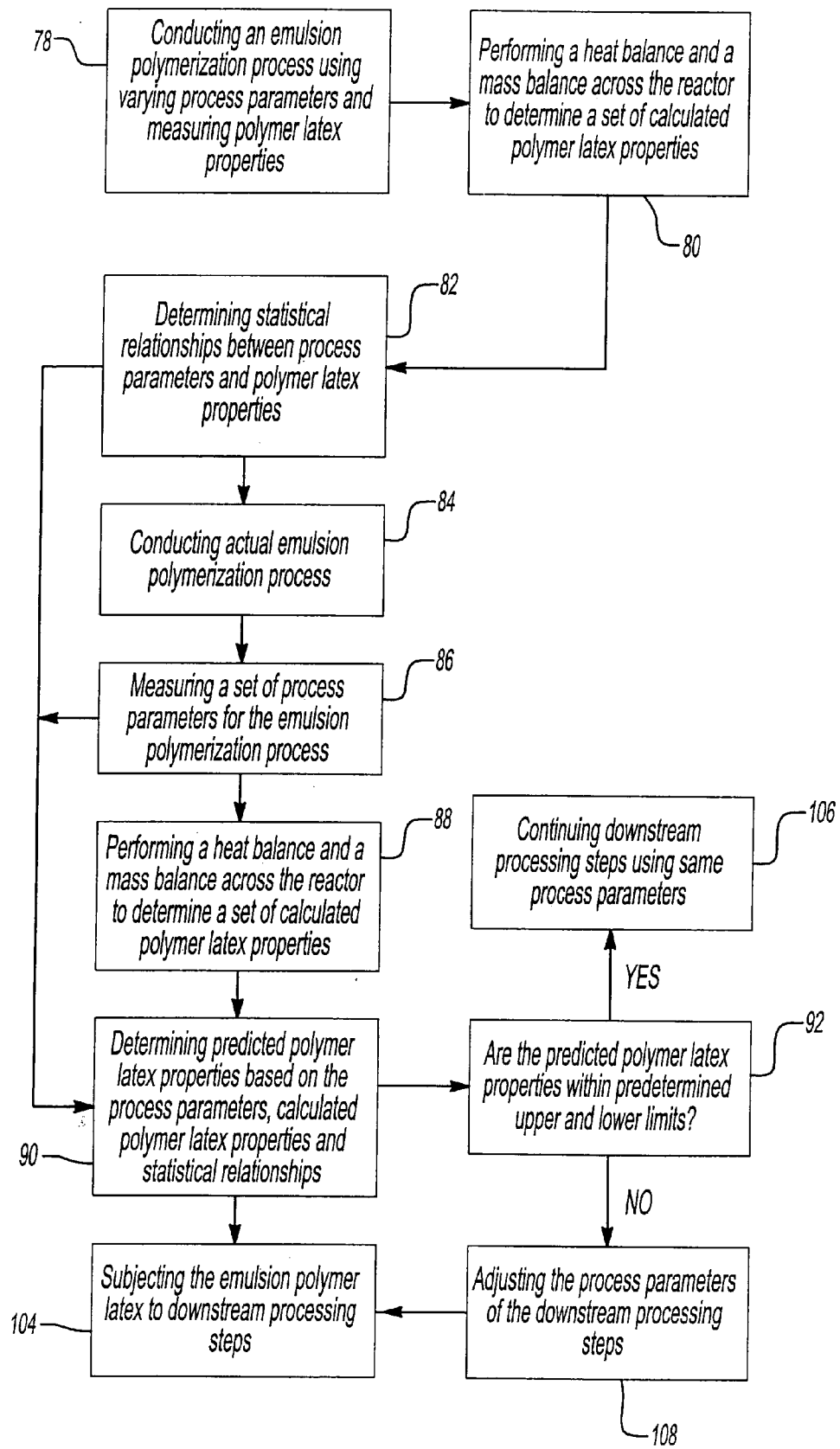
FIG. 5 is a flow diagram according to the invention illustrating the emulsion polymerization process, the method of predicting polymer latex properties, and the use of feed forward control to adjust the process parameters of processing steps downstream of the reactor if the predicted polymer latex properties are not within predetermined upper and lower limits.

FIG. 5 is a flow diagram illustrating an embodiment of the invention that includes subjecting the emulsion polymer latex to processing steps downstream from the reactor 12 as shown in step 104 and using the predicted polymer latex properties for feed forward control of the downstream processing units. Exemplary downstream processing units include the redox treatment unit 44, the steam stripping unit 46 and the agglomeration unit 48 illustrated in FIG. 1. In particular, processing means such as processor 38 can be used to verify that the predicted polymer properties are within predetermined upper and lower limits for the polymer properties as shown in step 92. If the predicted polymer properties are within the predetermined upper and lower limits, the downstream processing steps can be continued using the same process parameters as shown in step 106. However, if the predicted polymer properties are not within the predetermined upper and lower limits, the process parameters for the downstream processing steps can be adjusted as shown in step 108. For example, process parameters such as the flow rate of the redox chemicals and the treatment time for the latex in the redox treatment unit 44; the flow rate of the steam feed 56, the temperature of the steam feed, and the stripping time for the latex for the steam stripping unit 46; and the pressure of the agglomeration unit 48, can be adjusted in accordance with the invention. In particular, the processor 38 can determine what changes need to be made to the process parameters for the downstream processing steps and communicate the changes to the process control units 70, 72 and 74 corresponding to the downstream processing units, which in turn can communicate the changes to the redox treatment unit 44, the steam stripping unit 46 and the agglomeration unit 48.

Figure 6:
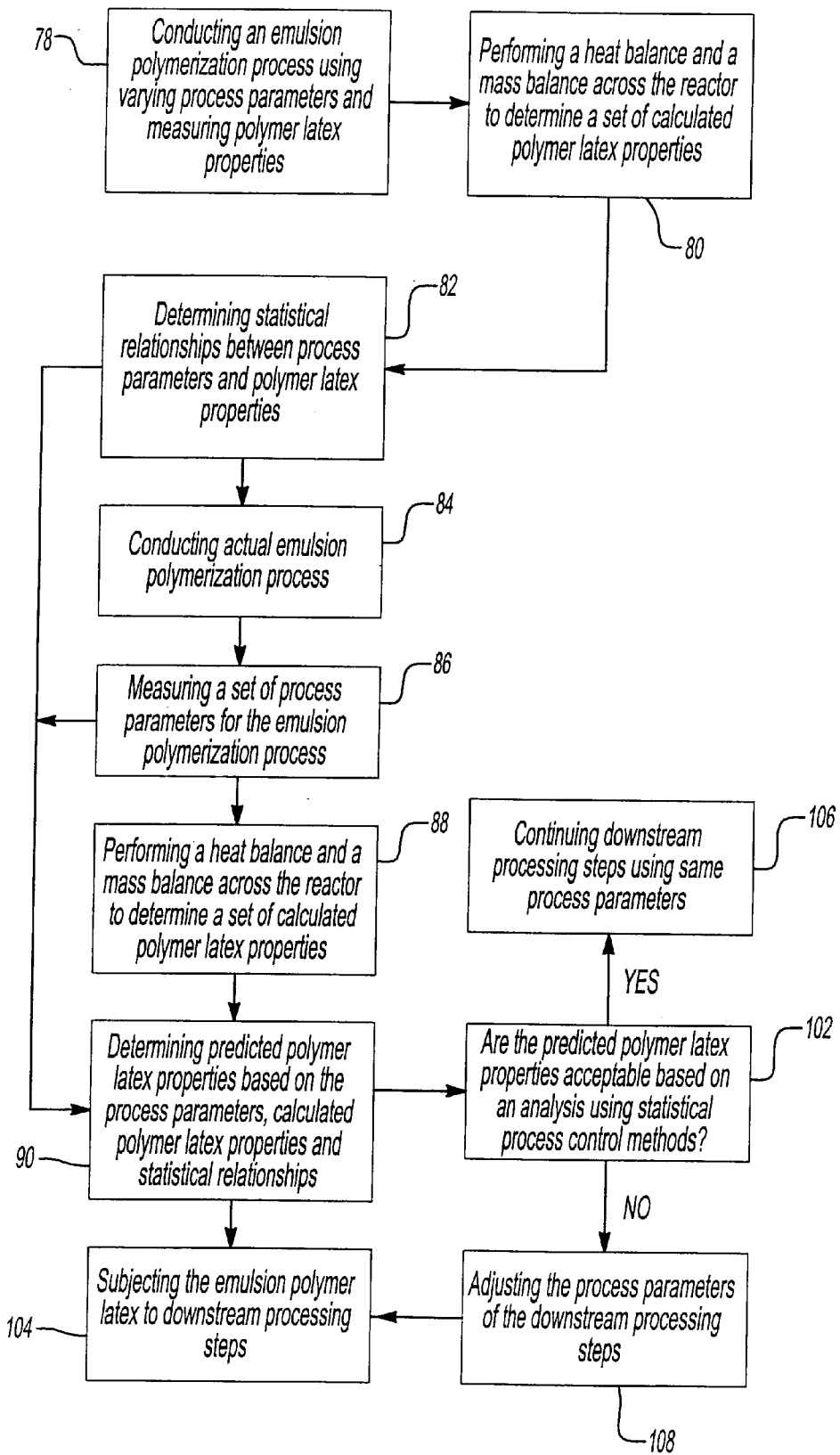
FIG. 6 is a flow diagram according to the invention illustrating the emulsion polymerization process, the method of predicting polymer latex properties, and the use of feed forward control to adjust the process parameters of processing steps downstream of the reactor if the predicted polymer latex properties are not acceptable based on a statistical process control analysis of the predicted polymer latex properties.

FIG. 6 is a flow diagram illustrating another embodiment of the invention that includes subjecting the emulsion polymer latex to processing steps downstream from the reactor 12 as shown in step 104 and using a statistical analysis of the predicted polymer latex properties to determine if feed forward control of the downstream processing units is desired. In particular, processing means such as processor 38 can be used to analyze the predicted polymer latex properties from step 90 using statistical process control methods known in the art to determine if the predicted polymer latex properties are acceptable as shown in step 102 and thus if the polymer latex is of acceptable quality. If the predicted polymer latex properties are acceptable, the downstream processing steps can be continued using the same process parameters as shown in step 106. However, if the predicted polymer properties are not acceptable, the process parameters for the downstream processing steps can be adjusted as shown in step 108. In particular, the processor 38 can determine what changes need to be made to the process parameters for the downstream processing steps and communicate the changes to the process control units 70, 72 and 74 corresponding to the downstream processing units, which in turn can communicate the changes to the redox treatment unit 44, the steam stripping unit 46 and the agglomeration unit 48.

As described above, the present invention includes several different components. It would be understood by those skilled in the art that these components can be implemented in several different ways. For example, the processor may consist of any number of devices. The processor may be a data processing device, such as a microprocessor or microcontroller or a central processing unit that executes the functions described above. In addition, although the present invention is described above with respect to one processor (processor 38 in FIG. 1), it would be readily understood by one skilled in the art that more than one processor could be used to implement the functions described above.

In addition to providing apparatus and methods, the present invention also provides computer program products for various functions such as performing a heat balance and a mass balance across the reactor 12 to determine calculated polymer latex properties; determining one or more predicted polymer latex properties for the emulsion polymer latex based on process parameters, calculated polymer latex properties, and statistical relationships between the process parameters and polymer latex properties; determining a set of statistical relationships between the process parameters and polymer latex properties based on varying process parameters and measured polymer latex properties; comparing the predicted polymer latex properties to predetermined upper and lower limits for the polymer latex properties; analyzing the predicted polymer latex properties using statistical process control methods to determine if the predicted polymer latex properties are acceptable and if process parameters for the emulsion polymerization process need to be adjusted; and the like. The computer program products have a computer readable storage medium having computer readable program code means embodied in the medium. The computer readable storage medium may be part of a memory device and may implement the computer readable program code means to provide the above functions.

FIGS. 2–6 are flow diagrams of methods, systems and program products according to the invention. It would be understood by those skilled in the art that the majority of the blocks or steps of the flow diagrams can be implemented by computer program instructions. These computer program instructions may be loaded onto a computer or other programmable apparatus to produce a machine, such that the instructions that execute on the computer or other programmable apparatus create means for implementing the functions specified in the flow diagrams. These computer program instructions can also be stored in a computer-readable memory that can direct a computer or other programmable apparatus to function in a particular manner, such that the instructions stored in the computer-readable memory produce an article of manufacture including instruction means which implement the function specified in the flow diagrams. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the flow diagrams.

Accordingly, the blocks or steps of the flow diagrams support combinations of means for performing the specified functions, combinations of steps for performing the specified functions and program instruction means for performing the specified functions. It will also be understood that each block or step of the flow diagrams, and combinations of blocks or steps in the flow diagrams, can be implemented by special purpose hardware-based computer systems which perform the specified functions or steps, or combinations of special purpose hardware and computer instructions.

The present invention will now be further described by the following non-limiting examples.

EXAMPLE 1

A number of emulsion polymers according to a specific recipe were produced using a semi-batch process in a reactor. The reactor was fitted with measuring instruments that provided values that were used to perform a heat and mass balance across the process. A suitably programmed computer calculated the heat and mass balance from these values and in turn calculated the monomer/polymer ratio (expressed as percent conversion). The output from the computer included the conversion (integrated with respect to time between 0.5 and 3.5 hours of the polymerization time), the reaction temperature (integrated with respect to time between 0 and 3.5 hours of the polymerization time), and the initial reaction temperature. The process was such that, by changing one process parameter, the particle size of the final polymer could be varied. For each polymerization, this process parameter had different values, and the final particle size of each batch was determined at completion. Table 1 shows the data obtained.

TABLE 1

| Integrated Conversion 0.5–3.5 hours (%) | Integrated Temperature 0–3.5 hours (° F.) | Initial Reaction Temperature (° F.) | Final Particle Diameter (Å) |
|---|---|---|---|
| 77.61 | 194.7 | 184.1 | 1567 |
| 70.93 | 193.9 | 189.4 | 1772 |
| 81.38 | 197.2 | 188.8 | 1503 |
| 83.86 | 194.6 | 187.2 | 1353 |
| 74.07 | 193.8 | 189.5 | 1583 |
| 76.96 | 193.6 | 181.8 | 1520 |
| 74.4 | 194.1 | 189.7 | 1700 |
| 76.66 | 195 | 187.1 | 1681 |
| 77.07 | 194.8 | 193.4 | 1659 |

Figure 7:
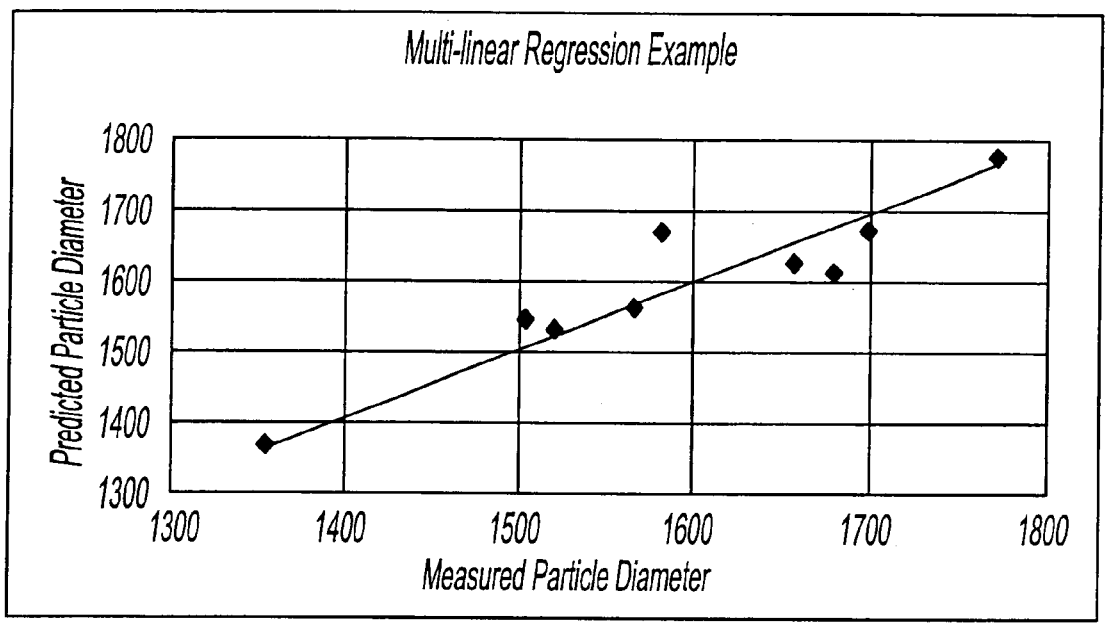
FIG. 7 is a multi-linear regression analysis of the measured particle diameter versus the predicted polymer diameter for an emulsion polymer that is used to determine a formula for the predicated particle diameter using the percent conversion, the integrated temperature and the initial temperature of the emulsion polymerization process.

The data in Table 1 was then subjected to a multi-linear regression analysis as illustrated in FIG. 7, with particle diameter as the dependent variable, to yield the following statistical relationship (with a correlation coefficient $R^2$ of 0.87):

$$\text{Particle Diameter} = -3749 - 33.49 \times \text{Conversion} + 35.75 \times \text{Integrated Temp.} + 5.12 \times \text{Initial Temp.}$$

EXAMPLE 2

Figure 8:
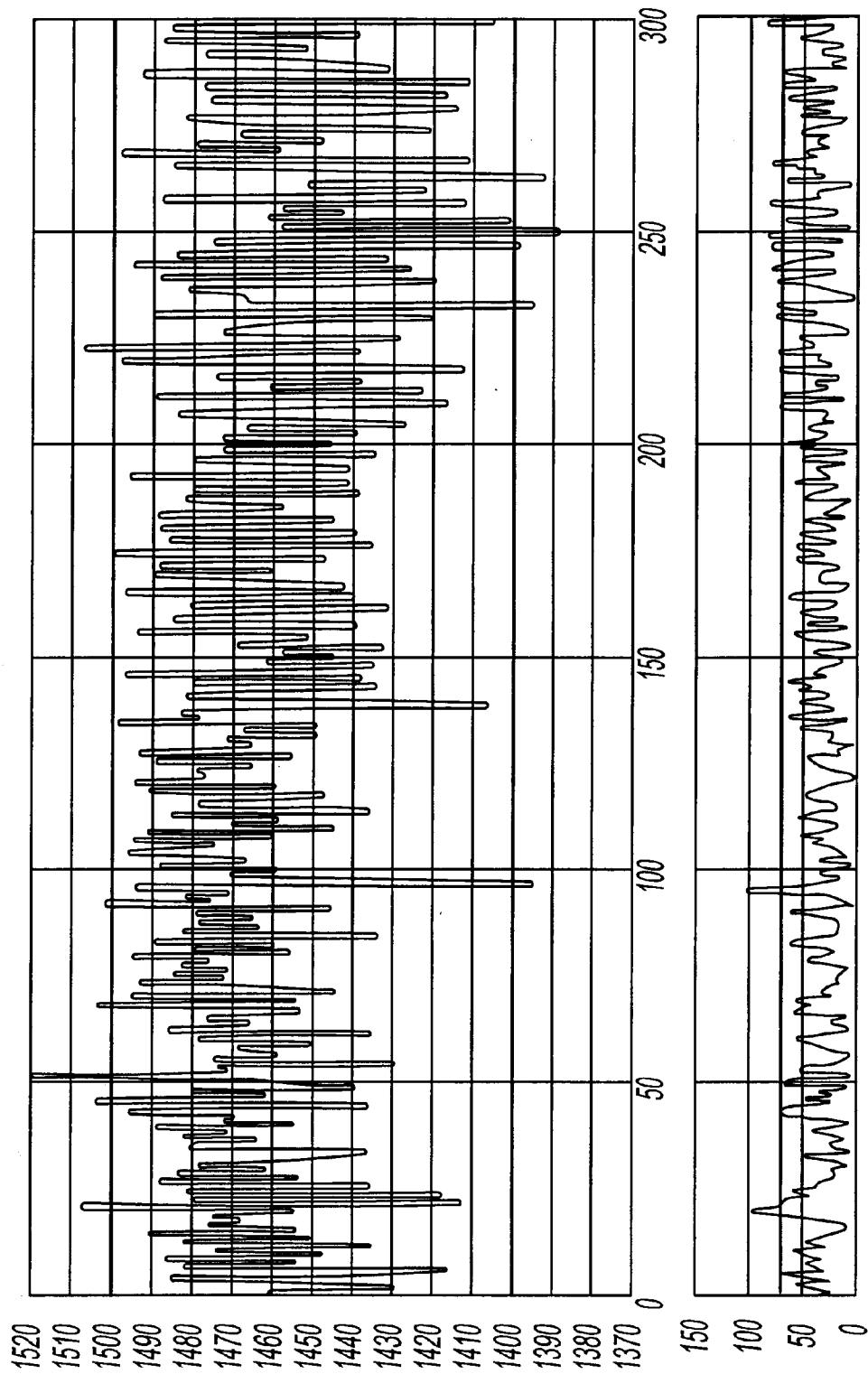
FIG. 8 is a graph of the predicted polymer size for an emulsion polymer over time and demonstrating times when the predicted polymer size was outside of predetermined upper and lower limits and tests of the emulsion polymer were conducted.

A specific emulsion polymer recipe was produced multiple times in three different reactors using a semi-batch process. The reactors were fitted with measuring instruments that provided values that were used to perform a heat and mass balance across the process. A suitably programmed computer calculated the heat and mass balance from these values and in turn calculated the monomer/polymer ratio (expressed as percent conversion). The output from the computer included the conversion (integrated with respect to time between 0.5 and 3.5 hours of the polymerization time), the reaction temperature (integrated with respect to time between 0 and 3.5 hours of the polymerization time), and the initial reaction temperature. Using a statistical relationship analogous to that derived in Example 1, a further suitably programmed computer predicted the particle diameter of each batch and compared the predicted value to predetermined lower and upper limits. Batches outside these limits were sampled for testing. As shown in FIG. 8, of the 300 batches made, six were predicted to be below the predetermined limits and five were predicted to be above the predetermined limits, giving a total of 3.7% of the batches that were tested.

EXAMPLE 3

Figure 9:
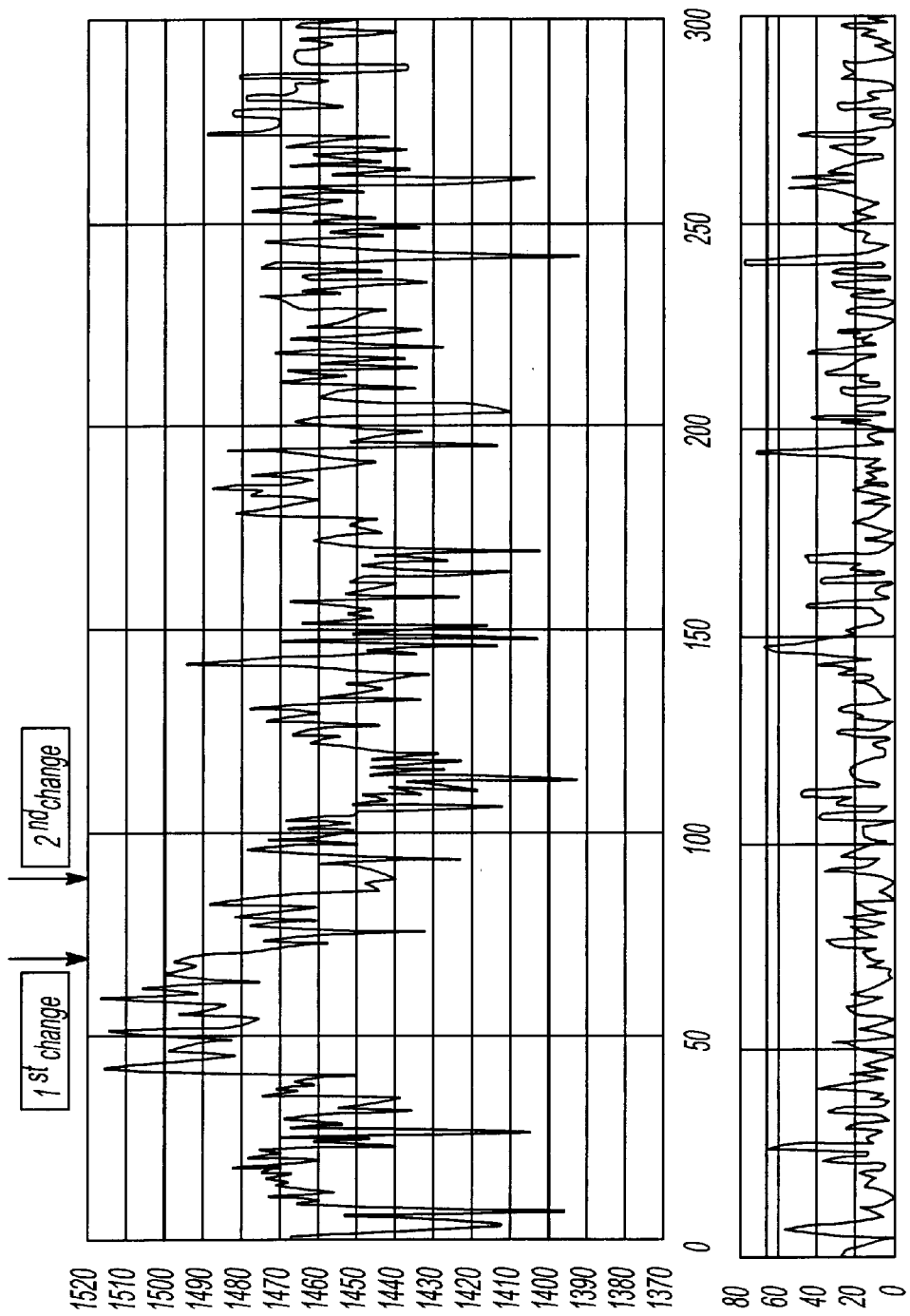
FIG. 9 is a graph of the predicted polymer size for an emulsion polymer over time and demonstrating times when undesirable trends in the predicted polymer size prompted a change in the process parameters.

A specific emulsion polymer recipe was produced multiple times in one reactor using a semi-batch process. The reactor was fitted with measuring instruments that provided values that were used to perform a heat and mass balance across the process. A suitably programmed computer calculated the heat and mass balance from these values and in turn calculated the monomer/polymer ratio (expressed as percent conversion). The output from the computer included the conversion (integrated with respect to time between 0.5 and 3.5 hours of the polymerization time), the reaction temperature (integrated with respect to time between 0 and 3.5 hours of the polymerization time), and the initial reaction temperature. Using a statistical relationship analogous to that derived in Example 1, a further suitably programmed computer predicted the particle diameter of each batch and plotted the predicted values on a control chart. After about 45 batches, an upward shift in the predicted particle size occurred as shown in FIG. 9. The higher values having been sustained for a number of batches, a change was made to one of the process parameters controlling particle size. The predicted particle size was reduced somewhat, and a second change in the process parameter was made to bring the predicted particle size closer to the target of 1450 as shown in FIG. 9.

The present invention provides a method for predicting polymer latex properties for an emulsion polymer latex based on statistical relationships between the polymer latex properties and process parameters. The method of the invention allows for real-time control of the emulsion polymerization process and thus facilitates the production of a quality emulsion polymer without the need to stop production for sampling and analytical testing. The method of the invention also provides feedback and feed forward control of the emulsion polymerization process to ensure the production of a quality product without increasing the cost of production. Furthermore, the method of the invention allows the operator to use the statistical relationships between polymer latex properties and process parameters for an emulsion polymerization process to predict the polymer latex properties for a second emulsion polymerization process making generally the same polymer.

It is understood that upon reading the above description of the present invention and the accompanying drawings, one skilled in the art could make changes and variations therefrom. These changes and variations are included in the spirit and scope of the following appended claims.

That which is claimed:

1. A method for predicting one or more polymer latex properties for an emulsion polymer latex, comprising the steps of:
    conducting an emulsion polymerization process in a reactor including one or more reactor inputs to produce an emulsion polymer latex;
    measuring a set of process parameters for the emulsion polymerization process;
    performing a heat balance and a mass balance across the reactor based on the set of process parameters measured in said measuring step to determine a set of calculated polymer latex properties for said emulsion polymerization process; and
    determining one or more predicted polymer latex properties for the emulsion polymer latex being prepared in the emulsion polymerization process using the set of process parameters, the set of calculated polymer latex properties, and a predetermined set of statistical relationships between the process parameters, the calculated polymer latex properties and the polymer latex properties to be predicted.

2. The method according to claim 1, wherein said conducting step comprises conducting an emulsion polymerization process in a reactor further including a coolant stream having an input and an output and said measuring step comprises measuring a set of process parameters that includes the mass of ingredients initially added to the reactor, the flow rates for the one or more reactor inputs, temperatures for the one or more reactor inputs, flow rates and temperatures for the coolant stream input and output, and the temperature and pressure of the reactor.

3. The method according to claim 2, wherein said performing step comprises performing a heat balance and a mass balance across the reactor based on the set of process parameters to determine the monomer/polymer ratio in the reactor.

4. The method according to claim 3, wherein said determining step comprises determining one or more predicted polymer latex properties for the emulsion polymer using the reactor temperature, the flow rates for the one or more reactor inputs, the monomer/polymer ratio and a predetermined set of statistical relationships between the reactor temperature, the flow rates for the one or more reactor inputs, the monomer/polymer ratio and the polymer latex properties to be predicted.

5. The method according to claim 1, further comprising the steps of:
    operating the emulsion polymerization process using a plurality of varying process parameters;
    measuring the polymer latex properties; and
    calculating a set of statistical relationships between the process parameters and polymer latex properties for the emulsion polymerization process based on the process parameters and measured polymer latex properties;
    wherein said one or more predicted polymer latex properties are determined using the set of statistical relationships from said calculating step.

6. The method according to claim 5, further comprising the step of performing a heat balance and a mass balance across the reactor using the varying process parameters from said operating step to determine a set of calculated polymer latex properties for said emulsion polymerization process; wherein said calculating step comprises calculating a set of statistical relationships between the process parameters and the measured and calculated polymer latex properties for the emulsion polymerization process.

7. The method according to claim 6, wherein said performing steps comprise performing a heat balance and a mass balance across the reactor to determine the monomer/polymer ratio.

8. The method according to claim 5, wherein said step of measuring process parameters comprises measuring process parameters selected from the group consisting of the reactor temperature and the flow rates for the one or more reactor inputs, and said step of measuring polymer latex properties comprises measuring polymer latex properties selected from the group consisting of monomer/polymer ratio, the number of polymer particles, the amount of polymer crosslinking, the molecular weight of the polymer, the concentration of Diels-Alder adducts and the polymer particle size.

9. The method according to claim 8, wherein said step of performing a heat balance and a mass balance comprises performing a heat balance and a mass balance across the reactor to determine the monomer/polymer ratio.

10. The method according to claim 9, wherein said determining step comprises using the monomer/polymer ratio from said performing step, the flow rates for the one or more reactor inputs, the reactor temperature and the statistical relationships from said calculating step to determine predicted polymer latex properties selected from the group consisting of the number of polymer particles, the amount of polymer crosslinking, the molecular weight of the polymer, the concentration of Diels-Alder adducts and the polymer particle size.

11. The method according to claim 1, further comprising the steps of:
comparing the predicted polymer latex properties from said determining step to predetermined upper and lower limits for the polymer latex properties;
taking a sample of the emulsion polymer latex from the reactor if the predicted polymer latex properties are not within the predetermined upper and lower limits for the polymer latex properties;
measuring the actual polymer latex properties from the sample to determine if the actual polymer latex properties are within the predetermined upper and lower limits; and
adjusting the process parameters for the emulsion polymerization reaction if the actual polymer latex properties are not with the predetermined upper and lower limits.

12. The method according to claim 1, further comprising the steps of:
comparing the predicted polymer latex properties from said determining step to predetermined upper and lower limits for the one or more polymer latex properties; and
adjusting the process parameters for the reactor if the predicted polymer latex properties from said determining step are not within the predetermined upper and lower limits for the polymer latex properties.

13. The method according to claim 1, further comprising the steps of:
analyzing the predicted polymer latex properties from said determining step using statistical process control methods to determine whether the predicted polymer latex properties are acceptable; and
adjusting the process parameters for the reactor if the predicted polymer latex properties from said determining step are not acceptable.

14. The method according to claim 1, further comprising the steps of:
subjecting the emulsion polymer latex produced from the emulsion polymerization to further processing steps;
comparing the predicted polymer latex properties from said determining step to predetermined upper and lower limits for the polymer latex properties; and
adjusting the process parameters for the further processing steps if the polymer latex properties from said determining step are not within the predetermined upper and lower limits for the polymer latex properties.

15. The method according to claim 14, wherein said subjecting step comprises subjecting the emulsion polymer to at least one processing step selected from the group consisting of a redox treatment step, a steam stripping step and an agglomeration step; and said adjusting step comprises adjusting at least one process parameter selected from the group consisting of the amount of redox chemicals in said redox treatment step, the addition time for the redox treatment step, the amount of steam in said steam stripping step, the stripping time in said steam stripping step, the temperature of said steam stripping step, the pressure in said agglomeration step, and the feed rate of the chemicals in said agglomeration step.

16. The method according to claim 1, further comprising the steps of:
subjecting the emulsion polymer produced from the emulsion polymerization to further processing steps;
analyzing the predicted polymer latex properties from said determining step using statistical process control methods to determine whether the predicted polymer latex properties are acceptable; and
adjusting the process parameters for the further processing steps if the polymer latex properties from said determining step are not acceptable.

17. The method according to claim 16, wherein said subjecting step comprises subjecting the emulsion polymer to at least one processing step selected from the group consisting of a redox treatment step, a steam stripping step and an agglomeration step; and said adjusting step comprises adjusting at least one process parameter selected from the group consisting of the amount of redox chemicals in said redox treatment step, the addition time for the redox treatment step, the amount of steam is said steam stripping step, the stripping time in said steam stripping step, the temperature of said steam stripping step, the pressure in said agglomeration step, and the feed rate of the chemicals in said agglomeration step.

18. The method according to claim 1, wherein said conducting step comprises conducting an emulsion polymerization process selected from the group consisting of continuous, batch and semi-batch emulsion polymerization processes.

* * * * *